(12) United States Patent
Middleton et al.

(10) Patent No.: US 7,639,847 B2
(45) Date of Patent: Dec. 29, 2009

(54) CORONARY ARTERY TREE IMAGING SYSTEM AND METHOD

(75) Inventors: Gardar T. Middleton, New Berlin, WI (US); John H. Jenkins, Grand Prairie, TX (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 1044 days.

(21) Appl. No.: 10/935,852

(22) Filed: Sep. 8, 2004

(65) Prior Publication Data

US 2006/0050941 A1   Mar. 9, 2006

(51) Int. Cl.
G06K 9/00 (2006.01)
(52) U.S. Cl. .................... 382/128; 382/130; 382/131; 382/154; 600/425; 600/428; 345/419; 345/424
(58) Field of Classification Search ............ 382/130, 382/154, 128, 131; 128/922; 345/419, 424; 600/425, 428; 378/4, 8, 15, 62, 95, 901
See application file for complete search history.

(56) References Cited

U.S. PATENT DOCUMENTS

| | | | | |
|---|---|---|---|---|
| 5,151,856 A | * | 9/1992 | Halmann et al. | 600/508 |
| 5,175,773 A | * | 12/1992 | Garreau et al. | 382/130 |
| 5,293,574 A | * | 3/1994 | Roehm et al. | 378/98.2 |
| 5,734,384 A | * | 3/1998 | Yanof et al. | 345/424 |
| 6,501,848 B1 | * | 12/2002 | Carroll et al. | 382/128 |
| 7,180,976 B2 | * | 2/2007 | Wink et al. | 378/8 |
| 7,189,208 B1 | * | 3/2007 | Beatty et al. | 600/587 |
| 7,321,677 B2 | * | 1/2008 | Evron et al. | 382/130 |

OTHER PUBLICATIONS

"3D+t Modeling of Coronary Artery Tree from Standard Non Simultaneous Angiograms", Fabien Mourgues et al., CHIR Team, INRIA, 2004.
"Automatic trinocular 3D reconstruction of coronary artery centerlines from rotational X-ray angiography" H.U. Lemke et al., CARS 2002.
"3-D Modeling and Mechanical Analysis of Moving Coronary Artery Tree in Vivo", Senhu Li et al.
"Rotational angiography and 3D coronary modeling: revolutions in the cardiac cath lab", J.T. Maddux et al., Medica Mundi, Aug. 2003.
"3D+t Modeling of Coronary Artery Tree from Standard Non Simultaneous Angiograms", Fabien Mourgues et al., CHIR Team, INRIA, Jan. 2004.
"Automatic trinocular 3D reconstruction of coronary artery centerlines from rotational X-ray angiography" H.U. Lemke et al., CARS 2002. Mar. 2002.
"3-D Modeling and Mechanical Analysis of Moving Coronary Artery Tree in Vivo", Senhu Li et al., Nov. 2006.

* cited by examiner

*Primary Examiner*—Vikkram Bali
*Assistant Examiner*—Nancy Bitar
(74) *Attorney, Agent, or Firm*—Andrus, Sceales, Starke & Sawall, LLP

(57) ABSTRACT

A method of generating an image of a coronary artery tree for a patient. The method can include acquiring data from the patient for coronary artery segments and generating a coronary artery tree image including the coronary artery segments. The method can also include accessing coronary artery tree patterns, comparing the coronary artery tree image to the coronary artery tree patterns, and automatically selecting one of the coronary artery tree patterns as a representative coronary artery tree image for the patient. The method can further include measuring lesions and automatically adding the lesion measurements to the coronary artery tree image for the patient.

22 Claims, 6 Drawing Sheets

CORONARY ARTERY TREE IMAGING SYSTEM AND METHOD

BACKGROUND OF THE INVENTION

The coronary artery tree is a system of arteries that supplies oxygen and nutrient-rich blood directly to the heart muscle. When these arteries begin to calcify, or build up fatty deposits along their walls, adverse cardiac events can occur, such as myocardial infractions or coronary artery disease. Proper diagnosis and treatment of these calcifications (also referred to as stenoses or lesions) are critical to reducing the high fatality rate associated with such adverse cardiac events.

Medical procedures, such as cardiac catheterization, generally result in reports created by the performing clinician that detail the procedure, including the diagnosis and the intervention performed. Such reports typically include graphics representative of the coronary artery tree pattern for the patient. Conventionally, the clinician creating the report must manually select an appropriate coronary artery tree pattern that represents the coronary anatomy of the patient. In addition, the clinician must remember the location and quantity of lesions in the patient's arteries or must manually input the lesion data into coronary annotation software.

Conventional imaging systems may include Quantitative Coronary Analysis (QCA) software. A clinician uses the QCA software during a QCA session to measure lesions in a patient's coronary arteries. Conventional imaging systems may also include coronary annotation software that is used to generate a coronary artery tree image for the patient. Currently, the clinician can use the coronary annotation software to only manually annotate the coronary artery tree image with information regarding lesions measured during the QCA session. The results of the QCA session currently cannot be saved and cannot be automatically transferred to the coronary annotation software for display on the coronary artery tree image for the patient. Also, conventional coronary annotation software only offers visual size interpretation of the lesions. In addition, the manual annotation and the visual size interpretation generally occur on different screens and at different times during the clinician's use of the coronary annotation software.

BRIEF DESCRIPTION OF THE INVENTION

In light of the problems and limitations described above, a need exists for the automatic input of the patient-specific data from QCA software into coronary annotation software in order to increase the efficiency and accuracy of coronary artery lesion mapping. Automatic input can eliminate or drastically reduce report time for the clinician, can ensure inclusion and accurate location of all lesions, and can ensure secure data transfer.

One embodiment of the invention includes a method of generating an image of a coronary artery tree for a patient. The method can include acquiring data from the patient for one or more coronary artery segments of the coronary artery tree, generating a coronary artery tree image including the coronary artery segments, and accessing coronary artery tree patterns. The method can also include comparing the coronary artery tree image to the coronary artery tree patterns using a pattern recognition module and automatically selecting one of the coronary artery tree patterns as a representative coronary artery tree image for the patient. The method can further include detecting a lesion in one of the coronary artery segments, and automatically adding a measurement of the lesion to the coronary artery tree image.

DETAILED DESCRIPTION

Figure 1:
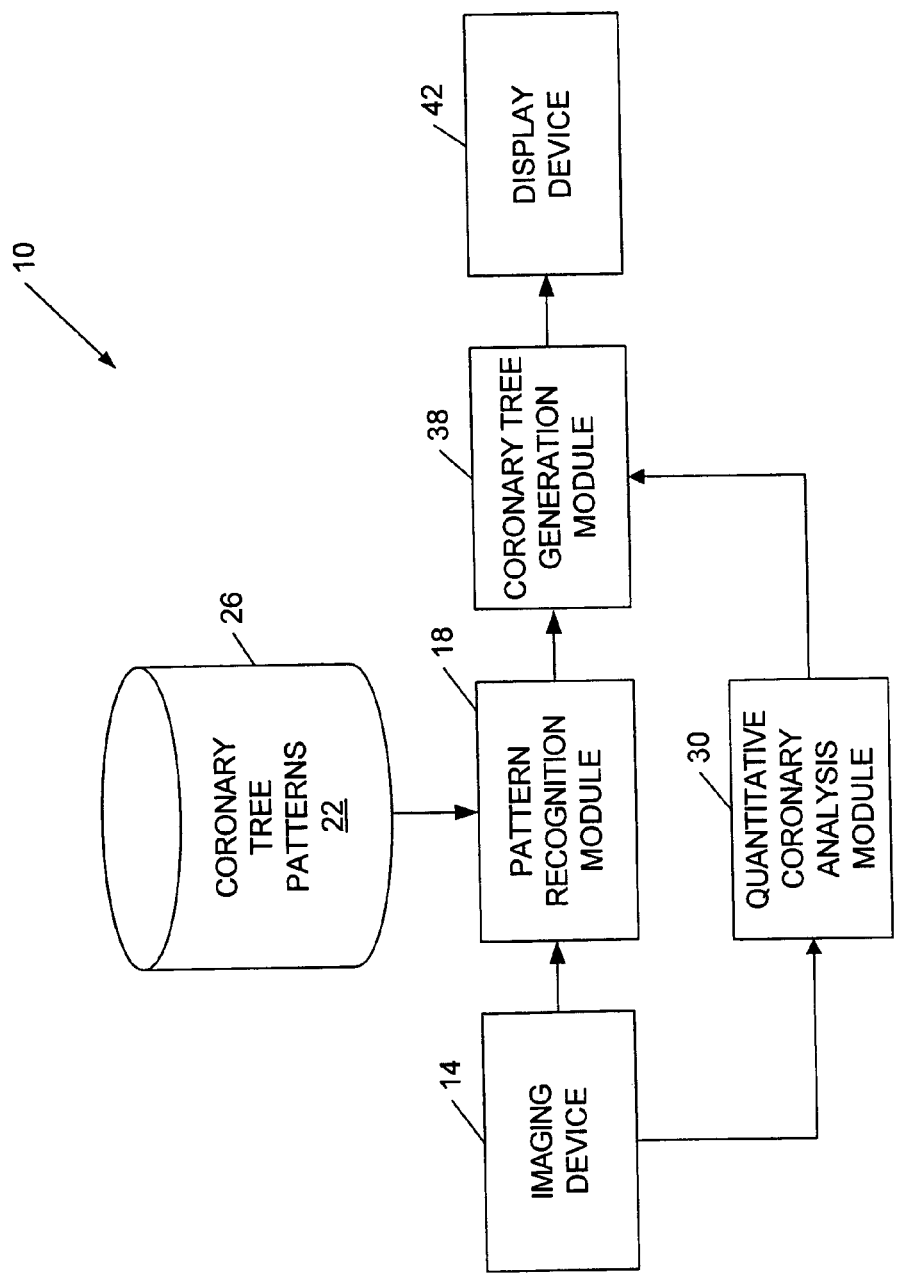
FIG. 1 is a schematic illustration of a coronary imaging system according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a coronary imaging system 10 according to one embodiment of the invention. The coronary imaging system 10 can include an imaging device 14, a pattern recognition module 18, coronary artery tree patterns 22 stored in a database 26, a quantitative coronary analysis (QCA) module 30, a coronary tree generation module 38, and a display device 42. The imaging device 14 can include any one or more of the following imaging devices: an x-ray machine, a magnetic resonance imaging system, a computerized axial tomography system, a digital imaging and communications in medicine (DICOM) image review system, and a positron emission tomography system. The imaging device 14 can acquire data from a patient in order to generate an original coronary artery tree image 34, as shown in FIGS. 3 and 4.

Figure 5:
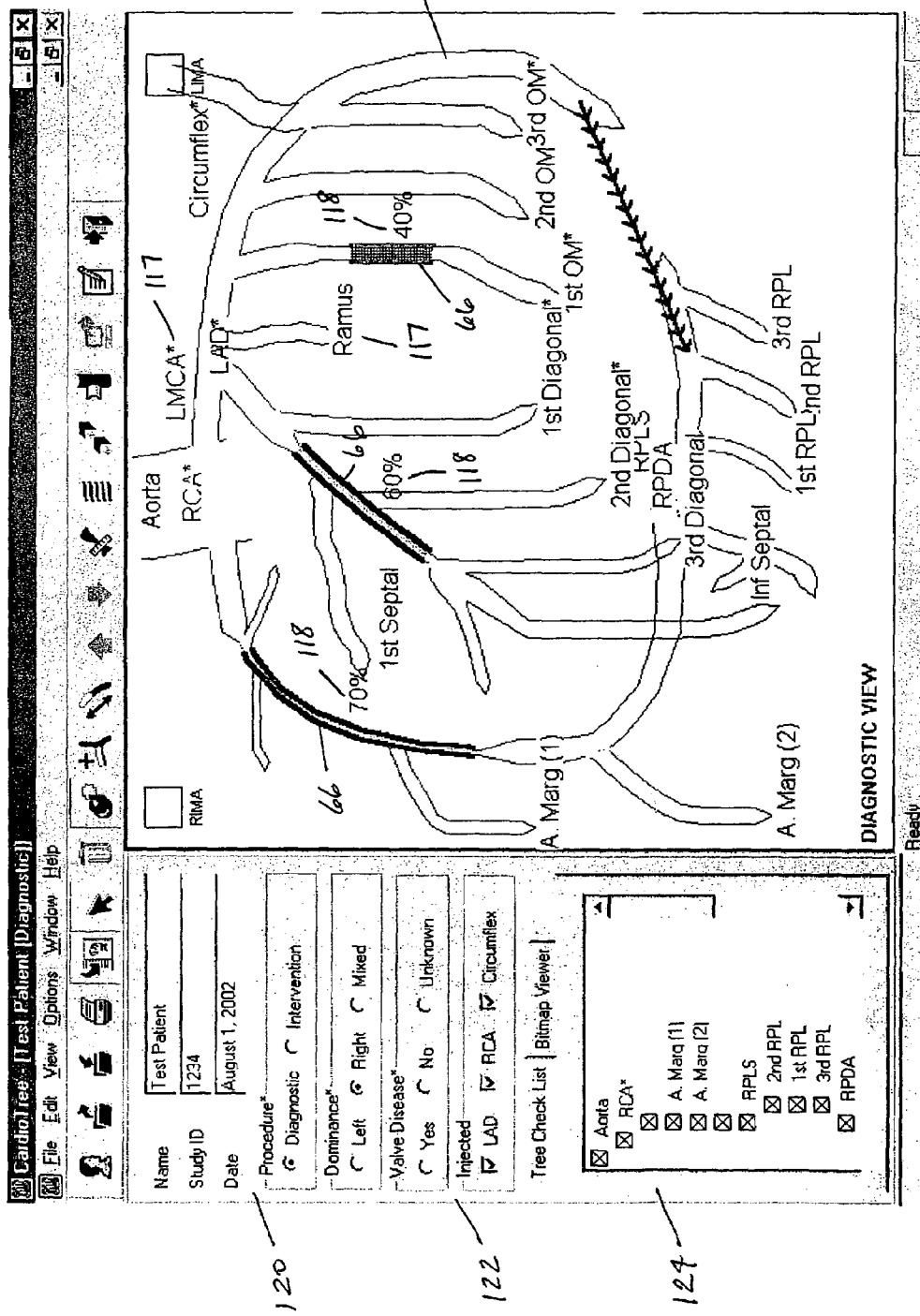
FIG. 5 is an illustration of a computer screen including an annotated coronary artery tree image that is displayed using the coronary imaging system of FIG. 1.

In some embodiments, the pattern recognition module 18 can access the coronary artery tree patterns 22 in the database 26. The database 26 can store coronary artery tree patterns 22 having a known condition, a known diagnosis, and/or a known physiology. Using pattern matching algorithms, the pattern recognition module 18 can compare the original coronary artery tree image 34 to the coronary artery tree patterns 22. In one embodiment, the pattern recognition module 18 can automatically select one of the coronary artery tree patterns 22 as a representative coronary artery tree that can be annotated to indicate the patient's lesions (as shown in FIG. 5). In some embodiments, the pattern recognition module 18 receives image positioning information from the imaging device 14 to assist in selecting the representative coronary artery tree pattern for the patient. In another embodiment of the invention, the pattern recognition module 18 can be omitted and the coronary tree generation module 38 can generate a coronary artery tree image including each coronary artery segment of the patient's actual coronary artery tree. In other words, rather than choosing a representative coronary artery tree that is similar to the patient's coronary artery tree, the coronary tree generation module 38 can generate a patient-specific coronary artery tree that is a replication of the patient's actual coronary artery tree. Whether the coronary artery tree image is a representative image or an actual image, an annotated coronary artery tree image 36 for the patient can be displayed as shown in FIG. 5.

Figure 3:
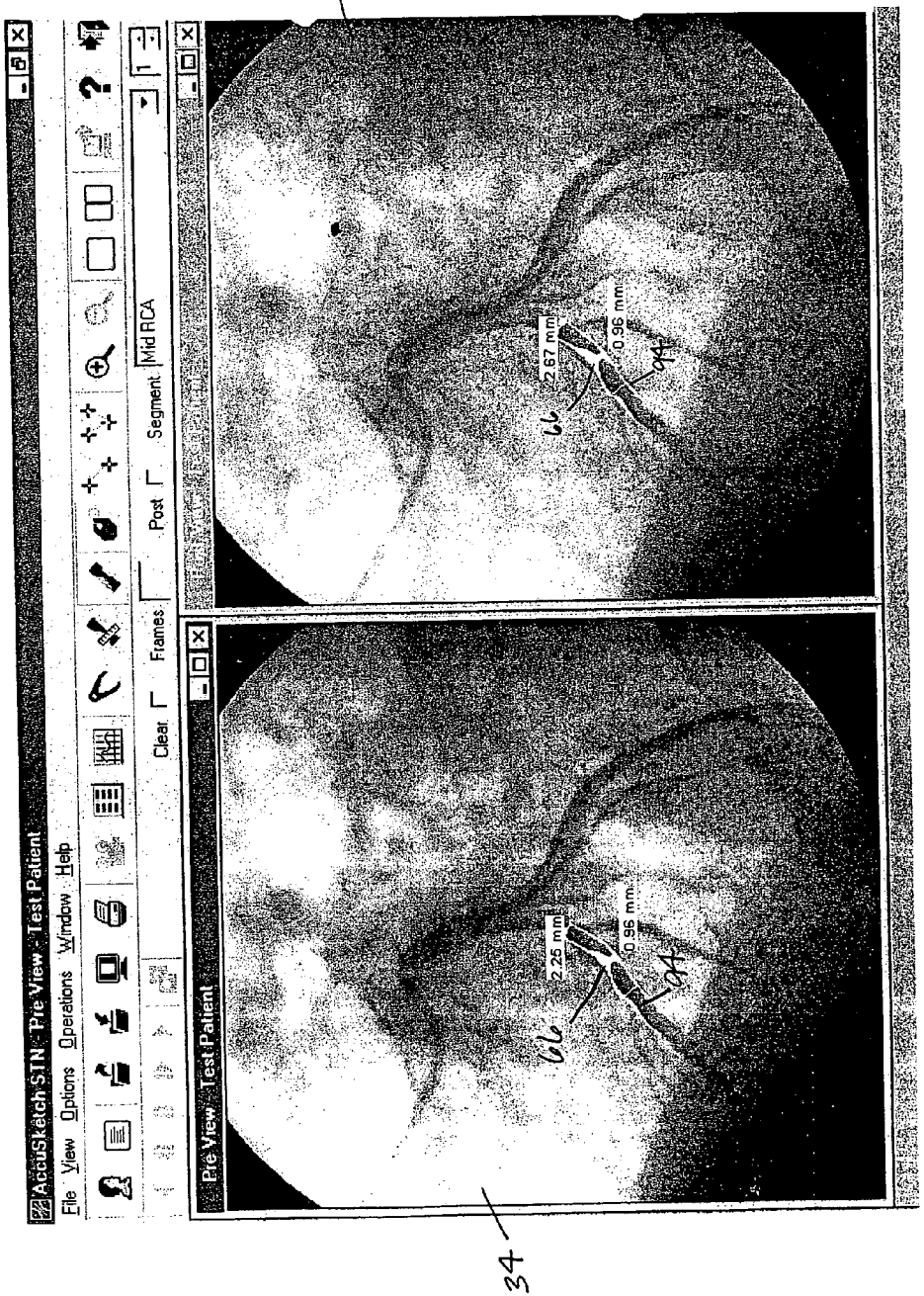
FIG. 3 is an illustration of a computer screen including original coronary artery tree images that are displayed using the coronary imaging system of FIG. 1.

Referring to FIG. 3, the QCA module 30 can be used by a clinician to measure any lesions shown in the original coronary artery tree image 34. The clinician can calibrate a measurement device of the QCA module 30 and can then use a mouse (or any other suitable pointer device) to select a lesion 66 located in a coronary artery tree segment 94. The QCA module 30 can detect the edge of the coronary artery and can measure the diameter and/or the cross-sectional area of the coronary artery along the length of the lesion, including the diameter at an obstructed point and the diameter at an unobstructed point. As shown in FIG. 3, the lesion 66 has resulted in a diameter of 0.96 mm at the most obstructed point. Also, the coronary artery has a diameter of 2.25 mm at an unobstructed point.

Figure 4:
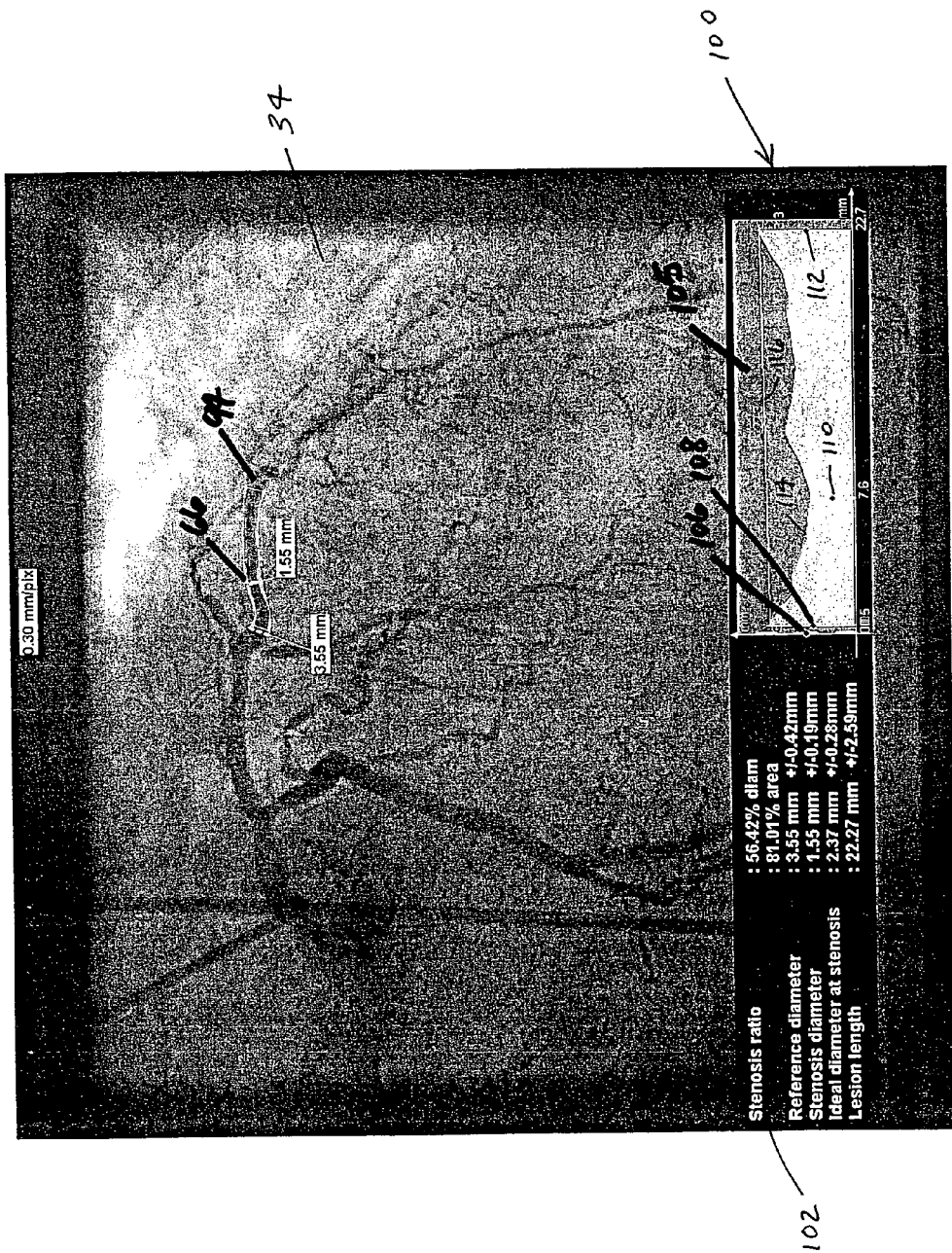
FIG. 4 is an illustration of a computer screen including a graphical user interface that is displayed using the coronary imaging system of FIG. 1.

The QCA module 30 or the coronary tree generation module 38 can generate a graphical user interface 100 (as shown in FIG. 4) for the display device 42. The graphical user interface 100 can include a list of parameters 102 and values 104 corresponding to each of the parameters 102. The parameters 102 can include stenosis ratio, reference diameter, stenosis diameter, ideal diameter at stenosis, and lesion length. The stenosis ratio parameter can include a first percentage (which is 56.42% in FIG. 4) indicating the amount by which the diameter of the coronary artery has been reduced by the lesion. The stenosis ratio parameter can include a second percentage (which is 81.01% in FIG. 4) indicating the amount by which the cross-sectional area of the coronary artery has been reduced by the lesion.

The graphical user interface 100 can also include an X-Y graph 105 with the X-axis representing a length of a coronary artery segment and the Y-axis representing a diameter of the coronary artery. For example, as shown in FIG. 4, the lesion is 22.27 mm long as represented by the X-axis of the X-Y graph 105. At its most unobstructed point, the coronary artery has a diameter of 3.55 mm as represented by a first data point 106. The beginning of the lesion can be represented by a second data point 108. The most obstructed point of the lesion can be represented by a third data point 110. At its most obstructed point, the coronary artery has a diameter of 1.55 mm, which is located 7.6 mm from beginning of the lesion and the first data point 106. The end of the lesion can be represented by a fourth data point 112, which is located 22.7 mm from the beginning of the lesion and the first data point 106. The X-Y graph 105 can also include a curve 114 that represents the change in diameter along the length of the lesion. In addition, the X-Y graph 105 can include a lesion length indicator 116 indicating that the lesion is 22.3 mm long.

The QCA module 30 can automatically provide data to the coronary tree generation module 38 through an internal software connection. In some embodiments, the coronary imaging system 10 includes an application program interface (API) that automatically reads and transmits the results of the QCA session to the coronary tree generation module 38. The QCA module 30 can automatically update the coronary tree generation module 38 with a patient-specific coronary artery tree image generated from actual measurements and accumulated analyses.

The coronary tree generation module 38 can output an annotated coronary artery tree image 36 (as shown in FIG. 5) to the display device 42. The annotated coronary artery tree image 36 can be displayed in a window with various menus for performing various tasks (such as the conventional save, open, and print functions, along with any other suitable functions). The annotated coronary artery tree image 36 can include labels 117 for many of the coronary arteries and other blood vessels (such as the aorta). A clinician can use the QCA module 30 or the coronary tree generation module 38 to assign a descriptor to each lesion from a drop-down list of lesion descriptors. A clinician can use the QCA module 30 or the coronary tree generation module 38 to place a comparable percentage stenosis mark 118 and/or a length measurement for each lesion on the annotated coronary artery tree image 36. In addition to the annotated coronary artery tree image 36, additional patient data 120, input fields 122, and a tree check list 124 can be displayed adjacent to the annotated coronary artery tree image 36. The additional patient data 120 can include the patient's name, a study identification, and a procedure date. The input fields 122 can include Procedure (Diagnostic or Intervention), Dominance (Left, Right, or Mixed), Valve Disease (Yes, No, Unknown), and Injected (LAD, RCA, and Circumflex). The tree check list 124 can include a listing of the coronary arteries that are currently displayed.

In some embodiments, the coronary tree generation module 38 automatically updates the annotated coronary artery tree image 36 with any lesions detected throughout the course of the QCA session. Upon completion or during the course of the QCA session, the clinician can view the annotated coronary artery tree image 36 shown in FIG. 5, including any descriptors, comparable percentage stenosis marks, and length measurements.

Figure 2A:
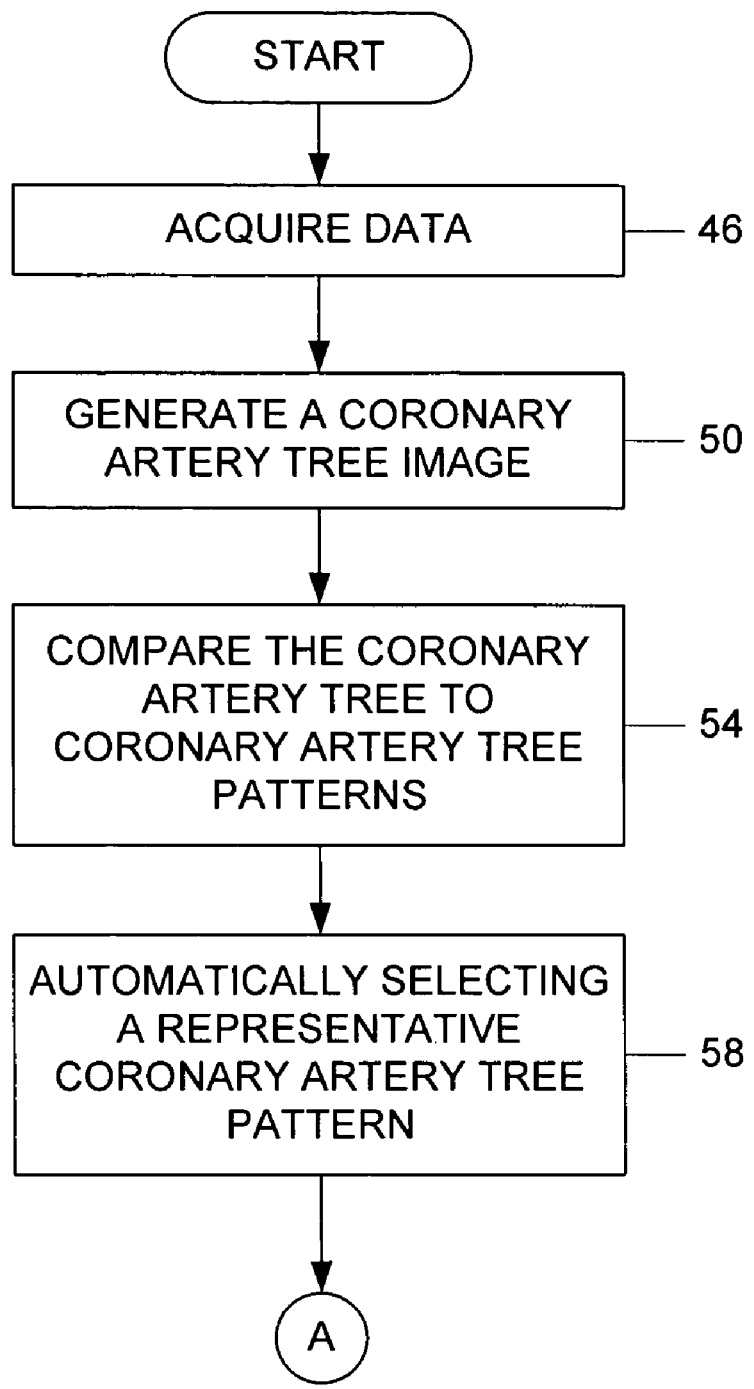
FIGS. 2A and 2B include a flowchart illustrating the operation of the coronary imaging system of FIG. 1 according to one embodiment of the invention.
Figure 2B:
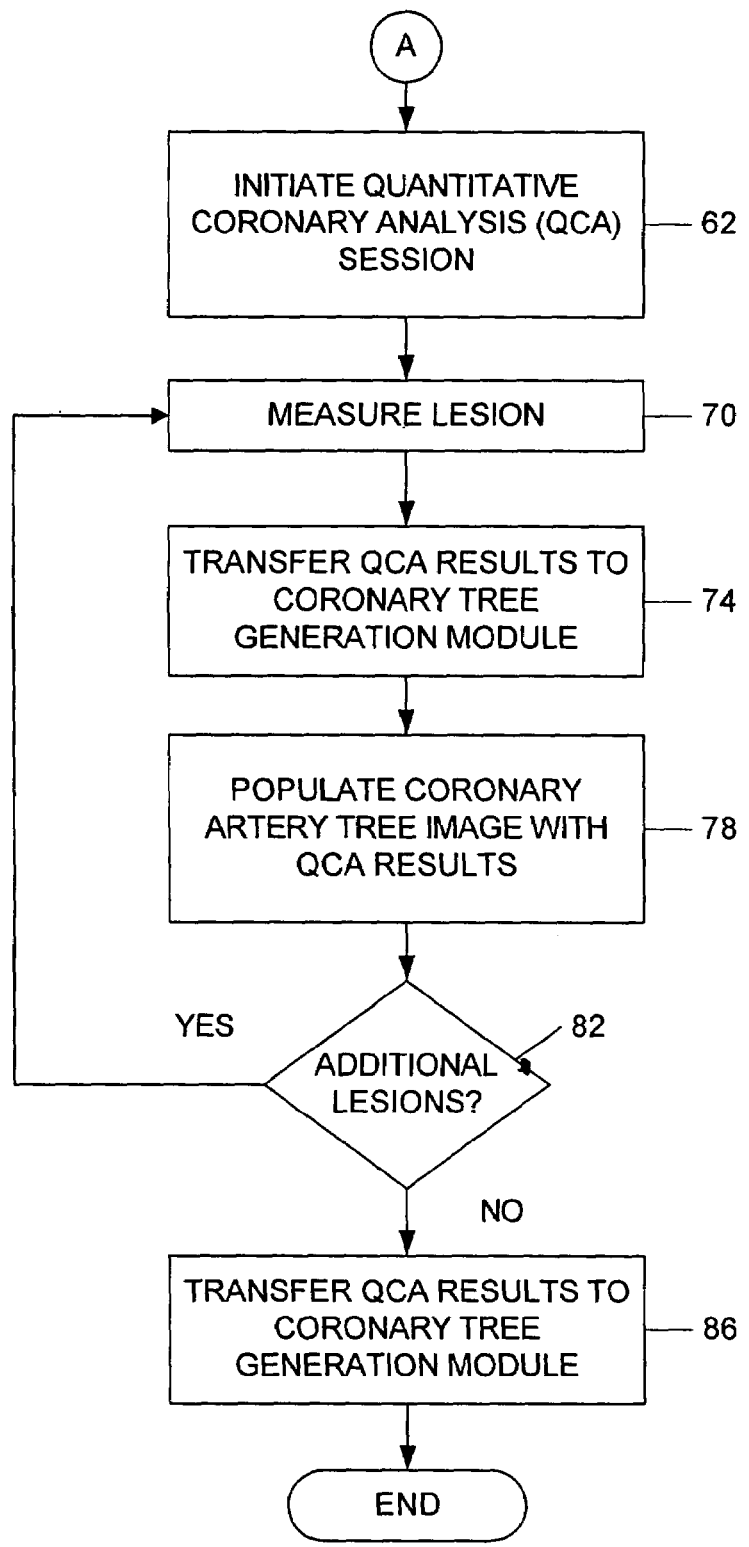

FIGS. 2A and 2B include a flowchart illustrating the operation of the coronary imaging system 10 according to one embodiment of the invention. The clinician can acquire (at 46) data from the patient using the imaging device 14. The imaging device 14 can generate (at 50) the original coronary artery tree image 34 (as shown in FIGS. 3 and 4). The pattern recognition module 18 can compare (at 54) the original coronary artery tree image 34 to the coronary artery tree patterns 22 stored in the database 26. The pattern recognition module 18 can automatically select (at 58) a representative coronary artery tree pattern for the patient.

Referring to FIG. 2B, the clinician can initiate (at 62) a Quantitative Coronary Analysis (QCA) session. The clinician can measure (at 70) a lesion 66 (as shown in FIG. 3). The QCA module 30 can automatically transfer (at 74) the results of the QCA session to the coronary artery tree generation module 38. The coronary tree generation module 38 can automatically populate (at 78) the annotated coronary artery tree image 36 (as shown in FIG. 5) with the results of the QCA session. In other words, the coronary tree generation module 38 can automatically add a measurement of the lesion 66 to the annotated coronary artery tree image 36 for the patient.

The clinician can use the QCA module 30 to determine (at 82) if there are additional lesions in the patient's coronary artery tree. If there are additional lesions, the QCA module 30 can measure (at 70) the additional lesions, transfer (at 74) the results, and populate (at 78) the annotated coronary artery tree image 36. If there are no additional lesions, the coronary tree generation module 38 can display (at 86) the annotated coronary artery tree image 36 populated with the lesions.

Various features and advantages of the invention are set forth in the following claims.

The invention claimed is:

1. A method of generating an image of a coronary artery tree for a patient, the method comprising:
    acquiring data from the patient with an imaging device for a plurality of coronary artery segments of the coronary artery tree; and
    executing a set of code embodied in a storage medium with a processor, such that the executed code effectuates the following steps:
    generating a coronary artery tree image on a display including the plurality of coronary artery segments;
    accessing a plurality of known and pre-existing coronary artery tree patterns from a coronary artery tree pattern database;
    comparing the coronary artery tree image to the plurality of known and pre-existing coronary artery tree patterns;
    automatically selecting one of the plurality of known and pre-existing coronary artery tree patterns that most closely matches the coronary tree image, wherein this selected coronary artery tree pattern is a representative coronary artery tree pattern image for the patient;
    displaying the representative coronary artery tree pattern image on the display; and
    measuring a lesion in one of the plurality of coronary artery segments and automatically adding a lesion measurement to the representative coronary artery tree pattern image on the display.

2. The method of claim 1 and further comprising accessing the plurality of known and pre-existing coronary artery tree patterns, each one of the plurality of known and pre-existing coronary artery tree patterns having at least one of a known condition, a known diagnosis, and a known physiology.

3. The method of claim 1 and further comprising acquiring data from the patient using at least one of an x-ray machine, a magnetic resonance imaging system, a computerized axial tomography system, a digital imaging and communications in medicine (DICOM) image review system, and a positron emission tomography system.

4. The method of claim 1 and further comprising comparing the coronary artery tree image to the plurality of known and pre-existing coronary artery tree patterns using a pattern recognition algorithm.

5. The method of claim 1 and further comprising displaying an X-Y graph for the lesion, the X-Y graph including an X-axis representing a length of the one of the plurality of coronary artery segments and a Y-axis representing a diameter of the one of the plurality of coronary artery segments.

6. A method of generating an image of a coronary artery tree for a patient, the method comprising:
    acquiring data from the patient with an imaging device for a plurality of coronary artery segments of the coronary artery tree; and
    executing a set of code embodied in a storage medium with a processor, such that the executed code effectuates the following steps:
    generating an original coronary artery tree image on a display including the plurality of coronary artery segments;
    acquiring imaging positioning information for at least one of the plurality of coronary artery segments;
    comparing the original coronary artery tree image to a plurality of pre-existing coronary artery tree patterns in a coronary artery tree pattern database;
    selecting a representative coronary artery tree pattern image from the plurality of pre-existing coronary tree patterns that most closely matches the original coronary artery tree image using the positioning information;
    displaying the representative coronary artery tree pattern image on the display; and
    adding a lesion measurement to the representative coronary artery tree pattern image on the display.

7. The method of claim 6 and further comprising acquiring data from the patient and imaging positioning information using at least one of an x-ray machine, a magnetic resonance imaging system, a computerized axial tomography system, a digital imaging and communications in medicine (DICOM) image review system, and a positron emission tomography system.

8. The method of claim 6 and further comprising displaying an X-Y graph for the lesion, the X-Y graph including an X-axis representing a length of the one of the plurality of coronary artery segments and a Y-axis representing a diameter of the one of the plurality of coronary artery segments.

9. A method of generating an image of a coronary artery tree for a patient, the method comprising:
    acquiring data from the patient with an imaging device for a plurality of coronary artery segments of the coronary artery tree;
    executing a set of code embodied in a storage medium with a processor, such that the executed code effectuates the following steps:
    generating a coronary artery tree image on a display including the plurality of coronary artery segments;
    comparing the coronary artery tree image to a plurality of preexisting coronary artery tree patterns from a coronary artery tree pattern database;
    selecting one of the plurality of preexisting coronary artery tree patterns that most closely matches the coronary tree image, wherein this selected coronary artery tree pattern is as a representative coronary artery tree pattern image for the patient;
    displaying the representative coronary artery tree pattern image on the display;
    detecting a lesion in one of the plurality of coronary artery segments; and
    automatically adding a measurement of the lesion to the representative coronary artery tree pattern image on the display.

10. The method of claim 9 and further comprising using a quantitative coronary analysis program embodied on a computer-readable medium to measure the lesion.

11. The method of claim 9 and further comprising assigning a descriptor to the lesion.

12. The method of claim 9 and further comprising placing at least one of a comparable percentage stenosis mark and a length measurement for the lesion on the representative coronary artery tree image.

13. The method of claim 9 and further comprising acquiring data from the patient and imaging positioning information using at least one of an x-ray machine, a magnetic resonance imaging system, a computerized axial tomography system, a digital imaging and communications in medicine (DICOM) image review system, and a positron emission tomography system.

14. The method of claim 9 and further comprising measuring a lesion in one of the plurality of coronary artery segments and automatically adding a lesion measurement to the representative coronary artery tree pattern image.

15. The method of claim 14 and further comprising displaying an X-Y graph for the lesion, the X-Y graph including an X-axis representing a length of the one of the plurality of coronary artery segments and a Y-axis representing a diameter of the one of the plurality of coronary artery segments.

16. The method of claim 9 and further comprising using an application program interface embodied on a computer-readable medium to automatically add the measurement of the lesion to the representative coronary artery tree pattern image.

17. A method of generating an image of a coronary artery tree for a patient, the method comprising:
generating a coronary artery tree image with an imaging device including a plurality of coronary artery segments using a coronary annotation program embodied on a computer-readable medium, wherein the coronary artery tree image is a representative coronary artery tree patterns image selected from a comparison between a patient image and a plurality of preexisting coronary tree patterns, wherein the comparison selects the most closely matching one of the plurality of pre-existing coronary tree patterns;
displaying the representative coronary artery tree pattern image on a display;
detecting a lesion in one of the plurality of coronary artery segments using a quantitative coronary analysis program embodied on the computer-readable medium;
automatically transmitting data between the quantitative coronary analysis program and the coronary annotation program in order to automatically add a measurement of the lesion to the coronary artery tree image; and
measuring a lesion in one of the plurality of coronary artery segments and automatically adding a lesion measurement to the annotated coronary artery tree image on the display, and wherein the coronary annotation program and the quantitative coronary analysis program embodied on the computer-readable medium, are executed with a processor, and further wherein the computer-readable medium further includes a set of additional executable code, that when executed effectuates the automatic transmitting and measuring steps.

18. The method of claim 17 and further comprising assigning a descriptor to the lesion.

19. The method of claim 17 and further comprising placing at least one of a comparable percentage stenosis mark and a length measurement for the lesion on the coronary artery tree image.

20. The method of claim 17 and further comprising acquiring data from the patient and imaging positioning information using at least one of an x-ray machine, a magnetic resonance imaging system, a computerized axial tomography system, a digital imaging and communications in medicine (DICOM) image review system, and a positron emission tomography system.

21. The method of claim 17 and further comprising displaying an X-Y graph for the lesion, the X-Y graph including an X-axis representing a length of the one of the plurality of coronary artery segments and a Y-axis representing a diameter of the one of the plurality of coronary artery segments.

22. The method of claim 17 and further comprising using an application program interface embodied on the computer-readable medium to automatically add the measurement of the lesion to the coronary artery tree image.

* * * * *

UNITED STATES PATENT AND TRADEMARK OFFICE
CERTIFICATE OF CORRECTION

| | | |
|---|---|---|
| PATENT NO. | : 7,639,847 B2 | Page 1 of 1 |
| APPLICATION NO. | : 10/935852 | |
| DATED | : December 29, 2009 | |
| INVENTOR(S) | : Middleton et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1225 days.

Signed and Sealed this

Ninth Day of November, 2010

David J. Kappos
*Director of the United States Patent and Trademark Office*